United States Patent [19]
Bach et al.

[11] Patent Number: 5,429,184
[45] Date of Patent: Jul. 4, 1995

[54] WOUND HEAT EXCHANGER OXYGENATOR

[75] Inventors: Ulf-Eiel F. Bach, Mound; Paul D. Brinda, Robbinsdale; Louis C. Cosentino, Deephaven, all of Minn.

[73] Assignee: Minntech Corporation, Minneapolis, Minn.

[21] Appl. No.: 254,632

[22] Filed: Jun. 8, 1994

Related U.S. Application Data

[63] Continuation-in-part of Ser. No. 219,432, Mar. 28, 1994, abandoned.

[51] Int. Cl.$^6$ .............................................. F28F 9/00
[52] U.S. Cl. ..................................... 165/149; 165/46; 165/173; 422/46; 422/48
[58] Field of Search .................. 165/46, 110, 149, 157, 165/161, 163, 172, 173, 175, 177; 128/DIG. 3; 422/46, 48

[56] References Cited

U.S. PATENT DOCUMENTS

| | | |
|---|---|---|
| 3,993,816 | 11/1976 | Baudet et al. . |
| 4,137,394 | 1/1979 | Meihuizen et al. . |
| 4,140,637 | 2/1979 | Walter . |
| 4,231,425 | 11/1980 | Engstrom ............................ 165/163 |
| 4,328,102 | 5/1982 | Bellhouse ............................. 165/46 |
| 4,336,138 | 6/1982 | Taniyama et al. . |
| 4,356,138 | 10/1982 | Kavesh et al. . |
| 4,368,124 | 1/1983 | Brumfield . |
| 4,413,110 | 11/1983 | Kavesh et al. . |
| 4,430,219 | 2/1984 | Kuzumoto et al. . |
| 4,559,999 | 12/1985 | Servas ................................... 165/163 |
| 4,572,446 | 2/1986 | Leonard et al. . |
| 4,622,206 | 11/1986 | Torgeson . |
| 4,689,255 | 8/1987 | Smoot et al. . |
| 4,761,864 | 8/1988 | Berger et al. . |
| 4,808,378 | 2/1989 | Nakanishi et al. . |
| 4,863,600 | 9/1989 | Leonard et al. . |
| 4,906,581 | 3/1990 | Baker et al. . |
| 4,911,846 | 3/1990 | Akasu et al. . |
| 4,940,617 | 7/1990 | Baurmeister . |
| 4,948,444 | 8/1990 | Schutz et al. . |
| 4,948,560 | 8/1990 | Deguchi et al. . |
| 4,975,247 | 12/1990 | Badolato et al. . |
| 5,120,501 | 6/1992 | Mathewson .................. 128/DIG. 3 |
| 5,135,804 | 8/1992 | Harpell et al. . |
| 5,137,531 | 8/1992 | Lee et al. . |
| 5,141,031 | 8/1992 | Baurmeister . |
| 5,143,312 | 9/1992 | Baurmeister . |
| 5,162,101 | 11/1992 | Cosentino et al. . |
| 5,186,832 | 2/1993 | Mancusi et al. . |
| 5,203,405 | 4/1993 | Gentry ................................... 165/161 |
| 5,224,522 | 7/1993 | Baurmeister . |
| 5,224,537 | 7/1993 | Potier ................................... 165/149 |
| 5,225,161 | 7/1993 | Mathewson ........................... 422/46 |
| 5,284,584 | 2/1994 | Huang et al. . |
| 5,289,873 | 3/1994 | Ryan ..................................... 165/149 |
| 5,297,591 | 3/1994 | Baurmeister . |
| 5,312,589 | 5/1994 | Reeder et al. . |
| 5,316,724 | 5/1994 | Mathewson et al. . |
| 5,352,361 | 10/1994 | Prasad et al. . |

FOREIGN PATENT DOCUMENTS

| | | |
|---|---|---|
| 3784549 | 4/1987 | Germany . |
| 2051667 | 1/1981 | United Kingdom . |
| 2217720 | 11/1989 | United Kingdom . |
| 2042414 | 9/1990 | United Kingdom . |

OTHER PUBLICATIONS

Gaylor, J. D. S., "Membrane Oxygenators: current developments in design and application," *J. Biomed. Eng*, 1988, vol. 10, Nov., pp. 541–547. Butterworth & Co.

(List continued on next page.)

*Primary Examiner*—Ira S. Lazarus
*Assistant Examiner*—Daniel J. O'Connor
*Attorney, Agent, or Firm*—Barbara A. Wrigley

[57] ABSTRACT

A low prime, high heat exchange efficiency oxygenator is provided which includes an oxygenation portion and a heat exchanger portion. Disposed within the heat exchanger portion is a hollow tube heat exchanger wound bundle which includes a plurality of hollow tubes knitted into a mat, the mat wound under tension into a bundle which includes from 16 to 24 layers of the mat. The oxygenator provided permits prime volumes of 180 to 240 mLs.

33 Claims, 3 Drawing Sheets

OTHER PUBLICATIONS

Richardson, P. D., et al., "Mass Transfer Through Tubes Wound in Serpentine Shapes," *Letters in Heat and Mass Transfer*, vol. 2, pp. 481–486, 1975. Pergamon Press, USA.

Drinker, Philip A., Ph.D., "Progress in Membrane Oxygenator Design," *Anesthesiology*, vol. 37, No. 2, Aug. '72, pp. 242–260.

Weng, Tin-Kan, "Transport and Flow Phenomena in a Microchannel Membrane Oxygenator," *Annals of Biomedical Engineering*, vol. 5, pp. 343–361, 1977. Academic Press, Inc.

Patankar, S. V. et al., "Prediction of laminar flow and heat transfer in helically coiled pipes," *J. Fluid Mech.*, vol. 62, part 3, pp. 539–551, 1974. Printed in Great Britain.

Komer, Claudia, MD, "Physiologic Changes of Cardiopulmonary Bypass," *Cardiopulmonary Bypass: Physiology, Related Complications, and Pharmacology*, Chapter 3, pp. 37–139, 1991. Futura Publishing Company, Mount Kisco, N.Y.

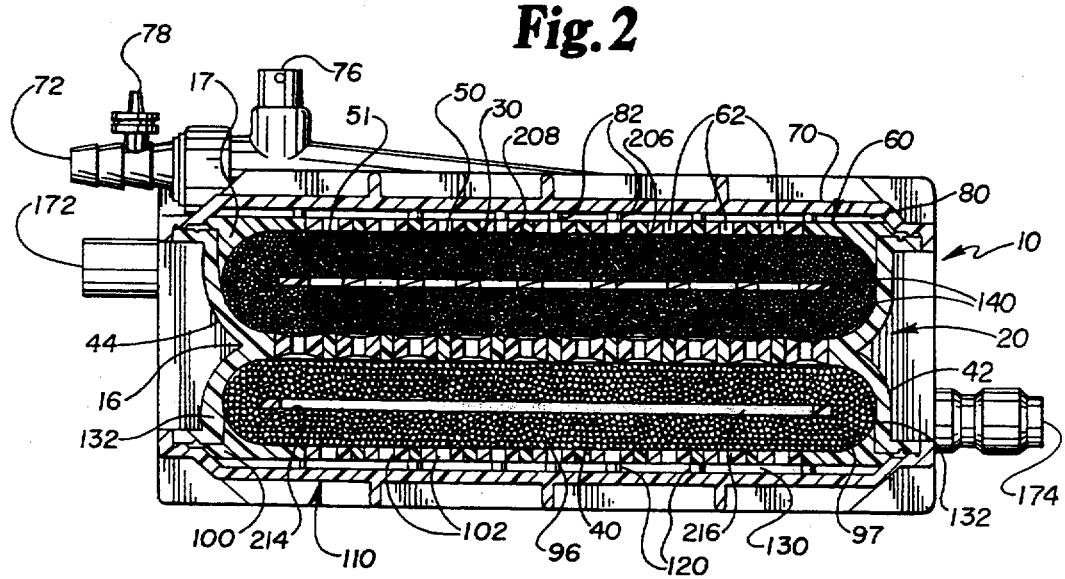
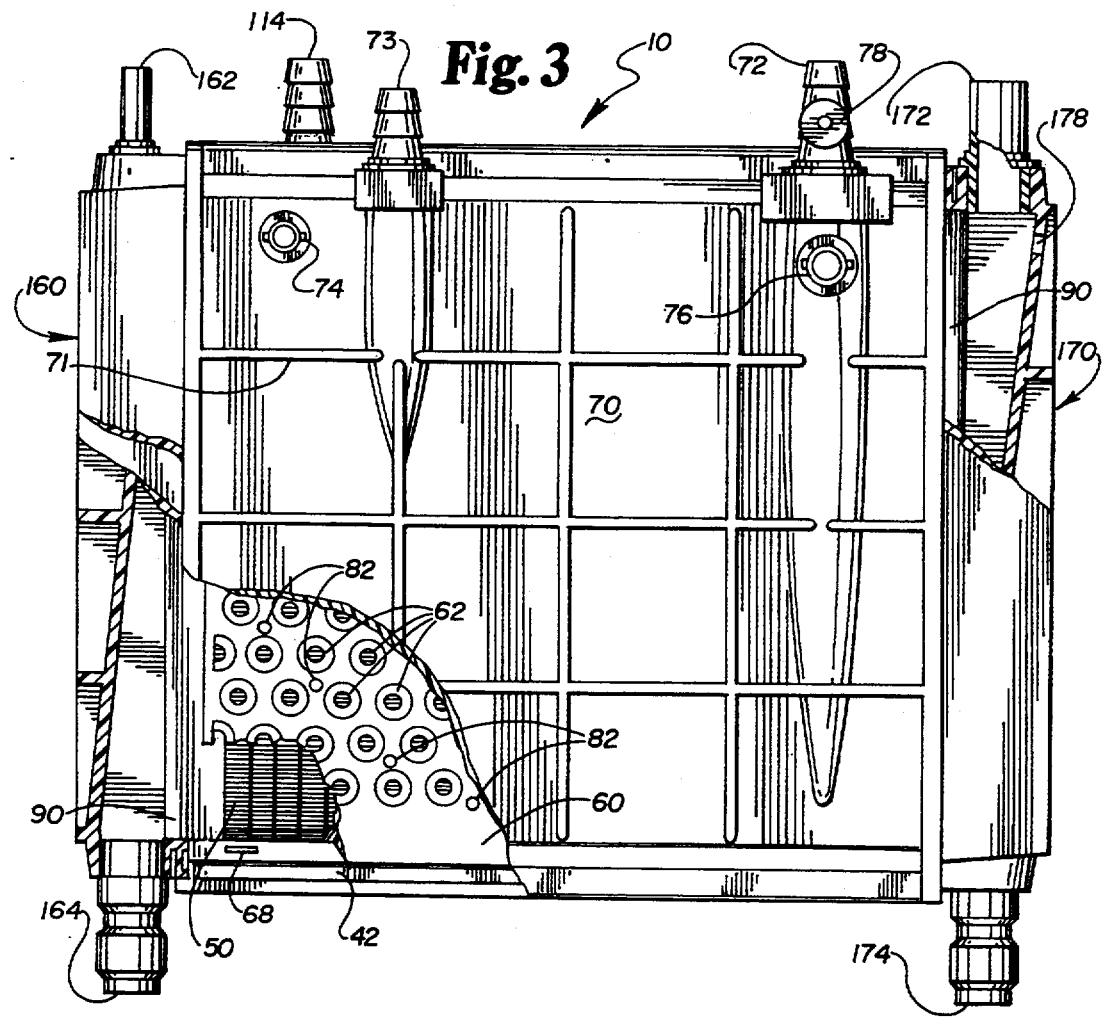

WOUND HEAT EXCHANGER OXYGENATOR

This application is a continuation-in-part of application Ser. No. 08/219,432 filed Mar. 28, 1994, now abandoned, the entirety of which is hereby incorporated by reference.

BACKGROUND OF THE INVENTION

1. Field of the Invention

This invention relates to the field of hollow fiber membrane type blood oxygenators. In particular, it relates to a unique design of hollow fiber membrane type oxygenators with a wound gas exchange membrane and a wound heat exchanger, which allows for a low prime volume, high gas transfer rate, high heat exchange efficiency and low pressure drop.

2. Description of the Related Art

From the first operation to repair a heart in 1891 until the early 1950s, heart surgeons were limited by the problem of trying to work on the heart while it was still beating. The heart's constant motion, and the presence of blood that obscured the surgeon's view, made repairing heart defects a surgical challenge. Surgeons had to work quickly and there was always a danger of disrupting blood circulation to vital organs. The solution to this problem came in the late 1950s with the development of the first oxygenators.

In nature, deoxygenated blood from the veins returns to the heart's right atrium. From the right atrium, blood is pumped to the right ventricle, then through the pulmonary artery to the lungs. The lung oxygenates the blood while removing carbon dioxide as it passes through the lung's alveolar capillary network. Oxygenated blood is then returned to the left atrium by way of the pulmonary veins. Blood is then pumped through the mitral valve into the left ventricle and pumped back into the body's circulatory system. Cells are replenished with oxygen and carbon dioxide is taken up by the blood as the blood passes through the body's capillary system. After this gaseous exchange is accomplished, the blood is returned to the heart and the cycle is repeated.

During cardiopulmonary surgery, venous blood is taken from the patient's circulation by means of a canula placed in the vena cavae. The blood "bypasses" the heart and lungs and enters what is referred to as the "extracorporeal circuit" or literally a circuit "outside the body." Oxygenation of the patient's blood takes place in an oxygenator much in the same way as it does in the natural process. After the blood is oxygenated and temperature regulated, it is returned to the patient's arterial circulation through a cannula so that the patient's body may utilize the oxygenated blood.

Ideally, therefore, oxygenators used in cardiopulmonary bypass surgery should emulate the natural process by ensuring that the blood is sufficiently oxygenated. In addition, an oxygenator must regulate the temperature of the blood and provide low pressure drops. Moreover, an oxygenator utilizing a low prime volume is desirable.

Prime Volume

Prime volume is the volume of liquid that the surgeon pumps through the extracorporeal system to "prime" it. Typically, prior to the initiation of surgery the total internal volume of the extracorporeal circuit, which includes the oxygenator, cardioplegia line, ventricular vent line, etc., must be primed. Priming is done to flush out any extraneous gas from the extracorporeal circuit prior to the introduction of the blood. The larger the priming volume, the greater the amount of priming solution present in the circuit which mixes with the patient's blood. The mixing of the blood and priming solution causes hemodilution. Hemodilution is disadvantageous and undesirable because the relative concentration of red blood cells must be maintained during the operation in order to minimize adverse effects to the patient.

In order to reduce the deleterious effects of hemodilution donor blood may be used. However, the use of donor blood is undesirable because while it reduces the disadvantages associated with hemodilution, donor blood presents complications such as compatibility and the potential transmission of disease. Alternatively, one may use hemoconcentrators to counter the effects of hemodilution. However, such devices add an additional cost to the procedure thus increasing an already expensive operation.

Another disadvantage of large prime volumes is the amount of time expended by the perfusionist in priming the circuit, which in turn increases the start-up time for surgery while operating personnel stand-by. The great majority of commercially available oxygenators have large prime volumes. Typically, the prime volume of the total extracorporeal circuit ranges from two to two and a half liters. Of that volume, the prime liquid in some commercially available oxygenators ranges from 550 mL to 750 mL such as that disclosed in U.S. Pat. No. 5,137,531 to Lee. It would be an advantage over commercially available oxygenators to provide an oxygenator that has a markedly reduced prime volume in order to overcome the disadvantages of commercially available, large prime units.

Reducing prime volume, however, affects other performance characteristics as well. For example, if prime is decreased by removing gas transfer fibers, oxygen transfer decreases, and the pressure drop decreases. If prime is decreased by increasing the pack density of the gas exchange fibers, oxygen transfer will increase, heat exchange efficiency will probably not be affected, but pressure drops will increase dramatically. If prime is decreased by reducing the available surface area of the heat exchange unit, oxygen transfer will not be affected but heat exchange efficiency will decrease. Therefore, one must carefully choose the design characteristics that will provide an oxygenator with a low prime volume, high oxygen transfer rates, high heat exchange efficiency and low pressure drops.

Oxygen Transfer

Most oxygenators utilize a bundle of hollow fiber membranes as the conduits for oxygen flow. In outside perfusion type blood oxygenators, the oxygen flows through the lumens of the hollow fibers while the blood flows on the exteriors. Blood is oxygenated because of the oxygen concentration gradient that exists between the oxygen gas present in the hollow fiber lumens and the blood surrounding the exterior of the fiber. High oxygen transfer rates are desirable to make as much oxygen available to the patient's system as possible.

Heat Exchange Efficiency

The patient enters the operating room at a body temperature of 37° C. Open heart surgery is performed at a temperature significantly lower than body temperature. High heat exchange efficiency, or the heat exchangers ability to transfer heat, is desirable to enable the perfusionist to bring the patient's body temperature down as quickly as possible as the blood passes through the heat exchanger and is recirculated back to the patient. If cooling is done too quickly, the patient's blood may coagulate. If cooling is done too slowly, the procedure becomes quite expensive as the entire operating team of surgeons, nurses and staff wait to start the procedure until the patient is sufficiently cooled.

Commercially available, larger heat exchangers with a large surface area of heat exchange coils or tubing are most efficient in performing the job. However, heat exchangers with large surface areas will inevitably utilize large amounts of prime volume. Therefore, most desirably, the heat exchanger must be as small as possible to minimize prime. A heat exchanger in which the surface area to volume ratio is large will minimize prime volume.

Pressure Drop

Pressure drop is the pressure differential between the blood inlet and the blood outlet port and measures the force that literally pushes the blood through the blood pathway of the oxygenator. High pressure drops stress component parts and connections of the oxygenator and may result in device failures that have potentially life-threatening effects on the patient.

A new and useful oxygenator is needed that overcomes the problems of commercially available units by providing (i) high heat exchange efficiency with reduced surface area; (ii) high oxygenation rates with reduced surface area; (iii) low pressure drops; (iv) markedly lower prime volumes by reducing the surface area of the gas transfer portion and reducing the surface to volume ratio of the heat exchanger portion but utilizing both portions more efficiently and (v) lower prime volumes by increasing the surface area to prime volume ratio.

SUMMARY OF THE INVENTION

It is an object of the wound heat exchanger oxygenator in accordance with the present invention to solve the problems outlined above that have heretofore inhibited attaining low prime volumes, high oxygenation rates, high heat exchange efficiency and low pressure drops. More particularly, the invention herein described provides a blood oxygenator that permits prime volumes of 180–240 mL, oxygen transfer rates of 350–440 mL/min, pressure drops of 60–120 mmHg when tested with fresh bovine blood (inlet to oxygenator) when the following conditions are met: total hemoglobin $12.0 \pm 1.0$ g/dl; percent oxygen saturation $55.0 \pm 2.0\%$; partial pressure carbon dioxide $45.0 \pm 5.0$ mmHg; base excess $0.0 \pm 2.0$ mmole/L; temperature $37.0 \pm 2.0°$ C.; activated clotting time greater than 480 seconds; and platelet count less than 100,000 $\mu$L.

The integrated heat exchanger and oxygenator in accordance with the present invention includes (a) a housing, the housing including first and second diffuser plates, a core with a perforated center divider having first and second opposing side walls, the core and the first diffuser plate together defining a first compartment and the core and the second diffuser plate together defining a second compartment; (b) a hollow fiber membrane wound bundle disposed within the first compartment including a plurality of hollow fiber membranes each defining a central lumen, the hollow fiber membrane wound bundle defining first and second hollow fiber end regions; and (c) a hollow tube heat exchanger wound bundle disposed within the second compartment including a plurality of hollow tubes each defining a central lumen, the hollow tube heat exchanger wound bundle defining first and second hollow tube end regions; (d) the hollow fiber end regions and hollow tube end regions being encapsulated with a potting compound which bonds to the first and second side walls; (e) first and second headers joined to the first and second opposing side walls; (f) first and second blood plates each joined to the opposing side walls of the core, wherein the first blood plate, the first diffuser plate and the potting compound define a blood collecting manifold and wherein the second blood plate, the second diffuser plate and the potting compound define a blood distribution manifold; (g) a blood inlet in fluid communication with the blood distribution manifold; (h) a blood outlet in fluid communication with the blood collecting manifold; (i) a heat exchanger media inlet and a heat exchanger media outlet in fluid communication with the lumens of the hollow tubes; and (j) a gas inlet and a gas outlet in communication with the lumens of said hollow fiber membranes.

The nonintegrated heat exchanger in accordance with the present invention includes (a) a housing, the housing including first and second perforated diffuser plates having first and second opposing side walls, the first and second diffuser plates and the first and second opposing side walls defining a heat exchange compartment; (b) a hollow tube heat exchanger wound bundle disposed within the heat exchange compartment, the hollow tube heat exchanger wound bundle including a plurality of hollow tubes each defining a central lumen, the hollow tube heat exchanger wound bundle having first and second hollow tube end regions; (c) the hollow tube end regions being encapsulated with a potting compound which bonds to the first and second side walls; (d) first and second blood plates each joined to the opposing side walls of the diffuser plates, wherein the first blood plate, the first diffuser plate and the potting compound define a blood collecting manifold and wherein the second blood plate, the second diffuser plate and the potting compound define a blood distribution manifold; (e) a blood inlet in fluid communication with the blood distribution manifold; (f) a blood outlet in fluid communication with the blood collecting manifold; and (g) a heat exchanger media inlet and a heat exchanger media outlet in fluid communication with the lumens of the hollow tubes.

One advantage of the present invention include prime volumes of 180–240 mL, oxygen transfer rates of 350–440 mL/min, pressure drops of 60–120 mmHg and heat exchange efficiency of from 40% to 55% thereby enhancing and facilitating patient recovery. The unique oxygenator in accordance with the present invention, provides another advantage by maximizing utilization of hollow fibers and hollow tubes while minimizing the actual surface area resulting in a significant cost savings to small manufacturing firms. Still another advantage of the present invention is that the lower overall surface area of hollow fibers decreases the likelihood of platelet and fibrinogen aggregation on the fiber surface and reduces the hemolysis rate of red blood cells.

BRIEF DESCRIPTION OF THE DRAWINGS

FIG. 2 is a cross sectional view of the oxygenator in accordance with the present invention;

FIG. 3 is a top plan view of the oxygenator of the present invention with parts cut away to show the wound hollow fiber membrane mat and the diffuser plate;

DETAILED DESCRIPTION OF THE PRESENTLY PREFERRED EXEMPLARY EMBODIMENTS

Figure 1:
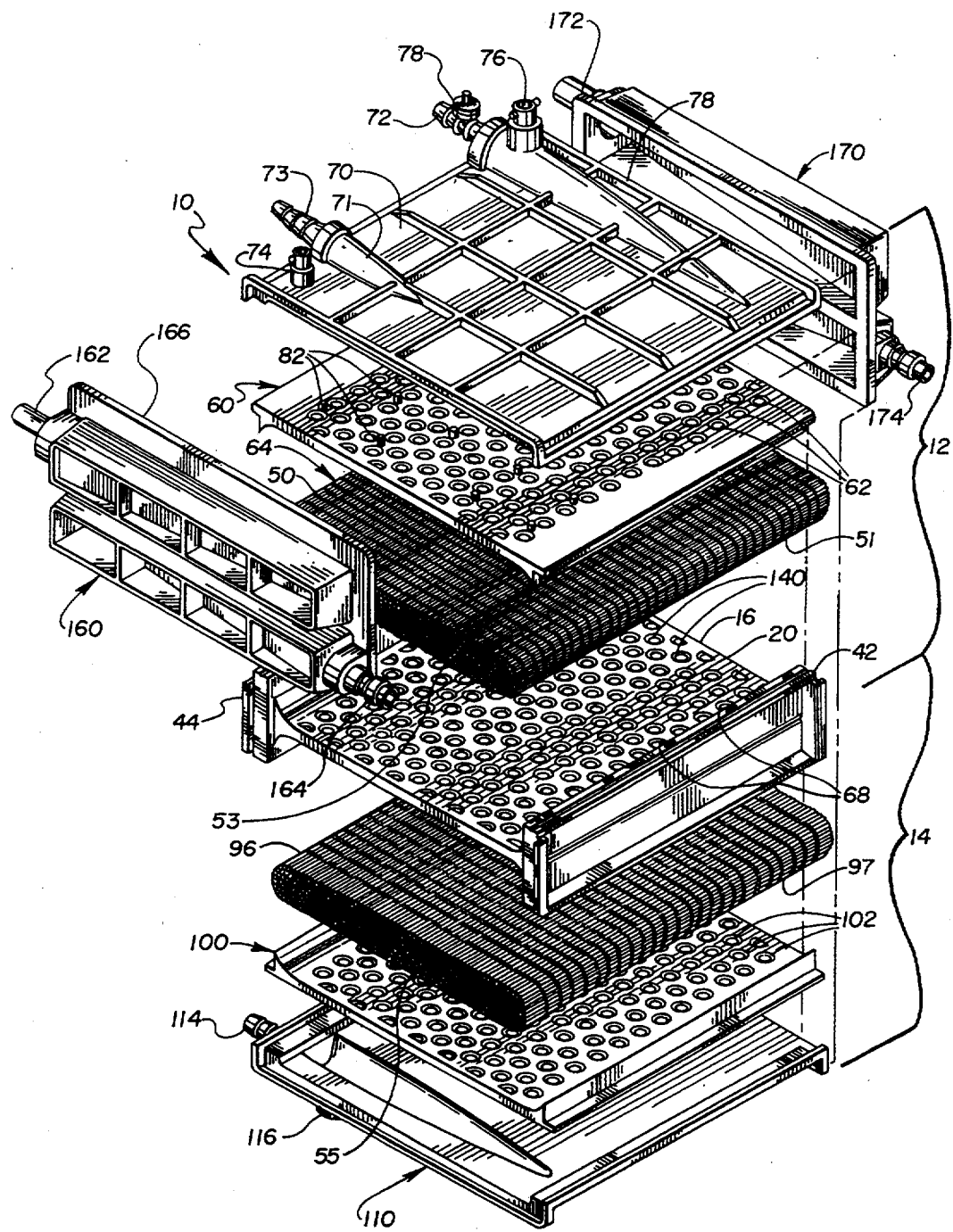
FIG. 1 is an exploded pictorial view of the oxygenator of the present invention.

FIGS. 1 and 2 depict the preferred embodiment of an oxygenator 10 with a wound heat exchanger in accordance with the present invention. Device 10 generally includes housing 17. Housing 17 includes first and second diffuser plates 60,100 and a generally H-shaped in cross section core member 20 which includes a perforated center divider 16 and first and second opposing side walls 42,44 defining a first compartment 30 and second compartment 40. Each compartment 30,40 is a longitudinally extending groove contained within housing 17. Center divider 16 forms the bridge between the outside legs 42,44 of the "H" of core member 20. First compartment 30 includes gas exchange (oxygenation) section 12 and second compartment 40 includes heat exchange section 14. Gas exchange section 12 and heat exchange section 14 are separated by a common center divider 16.

A. Gas Exchange Section

Figure 5:
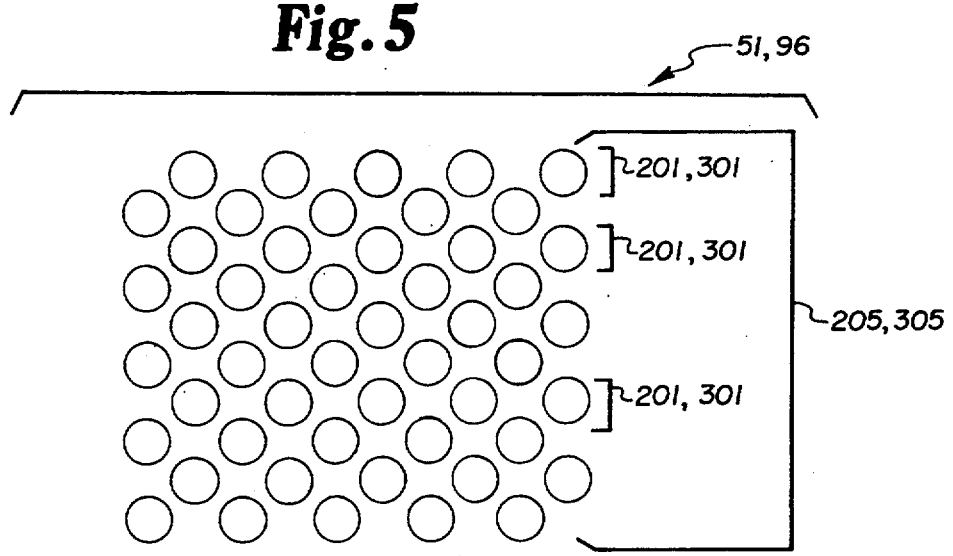
FIG. 5 is a schematic diagram of the wound hollow fiber membrane and/or tubing mats showing the spaced-apart pattern of interdigitation in accordance with the present invention.

Gas exchange section 12 includes the area defined by first compartment 30. First compartment 30 is filled with hollow fibers 50 knitted together into a mat as depicted in FIG. 5 and as more fully described below. The mat is then wound, as described more fully below, into a generally cylindrical to elliptical shape. The wound bundle is shown at 51.

Each of the hollow fibers 50 is a membrane designed for gas exchange. Each hollow fiber may comprise a porous resin capable of gas transfer such as polypropylene, polyethylene or other biocompatible suitable material which provides a gas exchange. The fibers are liquid impermeable. Suitable fibers for this purpose are well known and commercially available from a number of vendors including Mitsubishi Rayon Co., Ltd. of Tokyo, Japan and Celanese Chemical Co. of New York, N.Y.

A diffuser plate 60 as shown in FIGS. 1, 2 and 3 covers the upper ply of wound hollow fiber bundle 51 and is attached to legs 42,44 along its side edges. Diffuser plate 60 includes a plurality of chamfered orifices 62 which are spaced throughout the diffuser plate 60. Orifices 62 channel the passage of blood through plate 60 from first compartment 30. Plate 60 is constructed such that each orifice is chamfered to minimize sharp edges which might damage the hollow fibers.

The diffuser plate 60 bears against the wound hollow fiber membrane bundle 51 within first compartment 30.

The plate 60 assists in holding the hollow fibers at the desired pack density of fibers per unit area within the first compartment 30 and is also assisted in that purpose by cover 70. The chamfered orifices in plate 60 allow blood to pass through wound bundle 51 from diffuser plate 20 in a substantially planar manner. This provides optimum exposure of the blood to fiber surfaces and minimizes the pressure drop across the unit. It also aids in eliminating potential areas of stagnation which decreases efficiency and might give rise to clotting.

As stated previously, orifices 62 (and 102,140) are chamfered to enable the reduction of prime volume while still providing uniform flow distribution near the surface as well as control pack density. The inner diameter of chamfered orifices 62 (and 102,140 described below) are preferably from 0.625 inches (15.875 mm) to 0.0625 inches (1.59 mm), more preferably are 0.375 inches (9.53 mm) to 0.09 inches (2.28 mm), and most preferably are no larger than 0.125 inches (3.18 mm). The outer diameter of chambered orifices 62 (and 102,140) are preferably from 0.725 inches (18.42 mm) to 0.375 inches (9.53 mm) and most preferably no larger than 0.38 inches (9.65 mm).

Larger outer-diameter orifices than those referred to above reduce the ability of the plate to provide sufficient pack density control. In addition, larger outer-diameter, nonchamfered orifices reduce the ability of the plate 60 to provide pack density control and will allow the fibers to bulge into the orifices thereby potentially creating void spaces in the fibers which will reduce oxygenation because surface area is effectively reduced. More importantly, larger-diameter, nonchamfered orifices increase prime volume dramatically.

Chamfering the orifices allows one to reduce the total number of orifices in plate 60 (20 and 100) because the 0.38 inch (9.65 mm) outer diameter of the orifice controls pack density while the 0.125 inch (3.18 mm) inner diameter allows for a markedly reduced prime volume with no substantial effect on pressure drop, oxygen transfer rate or heat exchange efficiency.

The packing density of hollow fiber wound bundle 51 is generally calculated by the following formula:

$$\text{Packing Density (\%)} = \frac{\frac{\pi d^2 N}{4}}{(a \times b) + \frac{\pi b^2}{4}} \times 100$$

Where "d" represents the outer diameter of the hollow fibers (or hollow tubes as the case may be), "N" the number of hollow fibers (or hollow tubes) enclosed within the housing, "a" the inner width of the housing and "b" the inner height of the housing between the diffuser plate 60 (or 100) and center divider 16.

The preferred overall packing density of the hollow fiber membrane wound bundle 51 is between about 50% and 60%. Pack densities below about 45% show a substantial drop in performance and densities as low as 40% will result in channeling of blood. Packing densities of 40% exhibit visible channels through which blood is preferentially shunted. Such shunting prevents that blood from being fully oxygenated and carbon dioxide removal is also decreased. Packing densities greater than 60% result in hemolysis of the blood and decreased oxygen transfer rates. The preferred pack density described above will change with differences in fiber diameter.

Figure 6:
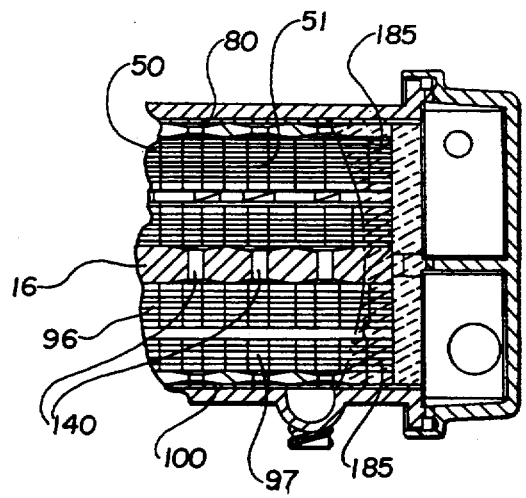
FIG. 6 is a partial cross-section of the present invention.

A first blood plate 70 vibration or heat welded onto core 20 further encloses the hollow fiber membrane wound bundle 51 as shown in FIGS. 1, 2 and 3. First blood plate 70 includes a blood outlet port 72 which preferably extends perpendicularly to the fibers across substantially the entire bundle as shown. Preferably, cover 70 also includes a vent port 74, temperature probe port 76, cardioplegia port 73 and a sample port 78. Sample port 78 may include a check valve/breather valve which allows a sample to be withdrawn without introducing air into blood collecting manifold 80. As shown in FIG. 6, first blood plate 70, diffuser plate 60 and potting compound 185 define blood collecting manifold 80. Blood collecting manifold 80 between first blood plate 70 and diffuser plate 60 is created by spacer nodes 82 and maintained in part due to the rigidity of diffuser plate 60. However, the force of maintaining the pack density of the fibers toward the diffuser plate tends to deform the highly perforated plate toward first blood plate 70. Therefore, a plurality of spacer nodes 82 are provided between first blood plate 70 and diffuser plate 60 to add strength to diffuser plate 60 to maintain pack density while providing superior blood flow distribution. First blood plate 70 is shown with a grid of outer ribs 71 to enhance the rigidity and strength of cover 70 but they are not essential.

1. Hollow Fiber Membrane Wound Bundle

Figure 4:
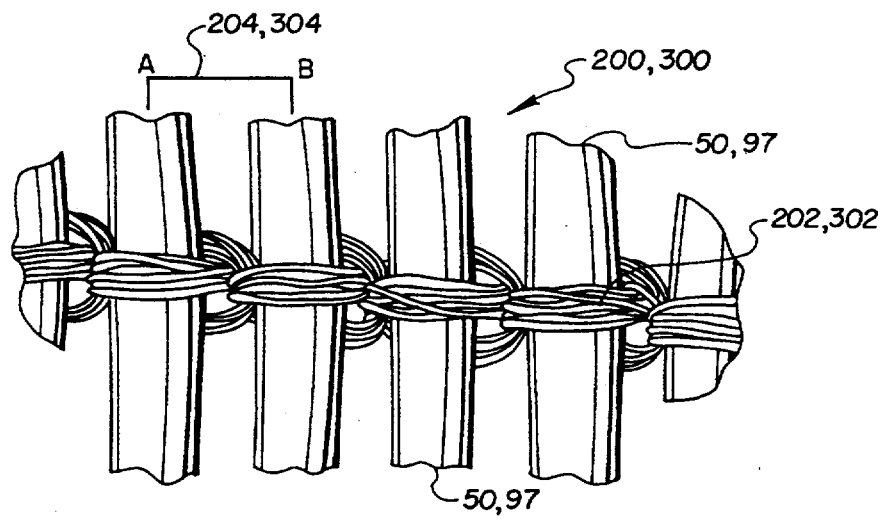
FIG. 4 is a schematic diagram of the matted hollow fiber membranes and/or matted hollow heat exchange tubes showing the spaced apart relationship between the fibers and tubes in accordance with the present invention.

Referring to FIG. 4, to maximize the performance characteristics of the oxygenator as a whole and to reduce prime volume, the present invention utilizes a weft knitted mat 200 of hollow fiber membranes 50, which is then wound into a hollow fiber membrane wound bundle 51.

Hollow fibers are knitted into a mat 200 by a weft knitting machine. A mat is a flat, single-layer arrangement of substantially parallel hollow fibers knitted together in a spaced apart relationship by warp thread means 202, as can be seen in FIG. 4. Weft knitting machines are well known in the textile industry and are used extensively to knit fabric and the like. Machines are available from American Liba Inc. (Piedmont, S.C.) and Karl Mayer Machine Corp. (Greensboro, N.C.).

Briefly, in constructing the mat a single strand of hollow fiber material is fed through a series of tension wheels with the tension preferably set at between 4–6 gms and most preferably at 5 gms. The strand of hollow fiber material is then threaded through a crochet needle positioned over warp thread means 202. Preferably from about 30–42 warp threads and more preferably 35–38 warp threads and most preferably 37 individual multi-stranded warp threads, spaced at a distance of 5 mm, are threaded through the eyelet needles of a warp placing rail. The eyelet needle segments installed on the warp placing rail move up and down, as well as laterally to the left and right.

Referring to FIG. 4, hollow fibers 50 are disposed at regular lateral intervals along the entire length of the mat 200. Hollow fibers 50 are knitted together and maintained substantially parallel to each other by warp thread means 202 running transversely to fibers 50. The warp thread means 202 may be a multi-filament thread or ribbon or tape.

The number of fibers per centimeter is preferably from 15.0 fibers to 21 fibers per centimeter, and most preferably is 19 fibers per centimeter. It is not necessary for the spacing interval 204 between each hollow fiber 50 to be identical so long as it falls within a range of approximately about 0.055 cm to 0.050 cm. The interval spacing is calculated by measuring the distance between center A and center B. In the preferred embodiment, the finished mat 200 is continuous.

The hollow fiber wound bundle is obtained by winding the continuous hollow fiber mat 200 described above onto a flat-shaped plate 206, seen in FIG. 2, under a winding tension of preferably 0.2–1.2 lbs and most preferably from 0.3–0.6 lbs. The plate 206 has a plurality of perforations 208 to enable transverse perfusion of the hollow fiber membrane wound bundle 51 while it is in place in compartment 30. In constructing wound bundle 51, hollow fiber mat 200 is partially wound by hand onto plate 206. The plate is placed on the winding arm of a tensioner/winding machine, readily available commercially. The tension is set at 0.6 lbs and the mat is wound for approximately 40 to 60 full revolutions or until one hollow fiber membrane wound bundle 51 preferably contains from about 80 to 120 layers of plies of the hollow fiber membrane mat 200. In the preferred embodiment, a hollow fiber membrane ply 201 is a fiber mat section formed in the production of the wound bundle per complete revolution of the bundle. Successive layers of hollow fiber plies 201 are stacked and maintained substantially parallel to each other with uniform spacing by the warp thread means 202. The individual hollow fibers 50 that comprise the plies 201 and layers 205 form a pattern of spaced apart interdigitation that allows for the uniform flow of blood thereby increasing oxygen transfer rate.

The number of layers 205 comprised of plies 201 that each hollow fiber membrane wound bundle 51 contains may vary within the limits described above depending upon the geometry of the gas transfer compartment into which it is inserted. For example, in a gas transfer compartment 30 in accordance with the present invention, a hollow fiber membrane wound bundle 51 preferably contains from about 90 to 100 layers of plies. However, if an oxygenator/heat exchanger is not needed as an integrated unit and rather it is desired to construct a nonintegrated gas transfer unit, one may make various changes to the geometry of the gas transfer compartment without deviating from the spirit of the present invention. For example, the width and height of the compartment may be varied and thus fewer than 90 layers of plies or more than 100 layers of plies may be needed. However, typically in order to have a sufficient gas transfer rate the layers of plies of hollow fiber membrane mat will be approximately from about 80–120.

The cross section of the hollow fiber membrane wound bundle so formed preferably has generally the form of a rectangle with rounded corners, a segment of a circle or semi-circle with rounded edges, or an ellipse. These types of shapes produce space-saving configurations and prime volume-reducing wound hollow fiber membrane bundle. After the potting procedure is completed, the rectangular portion of the hollow fiber membrane wound bundle encompasses the functional area while the rounded edges are nonfunctional because the higher pack density on the sides causes substantial resistance to flow.

As can be readily seen from FIGS. 4 and 5, the warp thread means 202 acts as a spacer between each parallel hollow fiber 50 in the mat 200 and each layer of hollow fiber mat that comprises the hollow fiber wound bundle. The advantage of this spaced apart relationship between the individual hollow fibers 50, each successive hollow fiber ply 201 and the layers 205 of plies of hollow fiber mat 205 is to control the distribution of blood flow so that it is uniform throughout the entire wound bundle 51. In other words, each red blood cell flowing through the oxygenator 10 has the possibility of being maximally oxygenated because of the great likelihood that it will contact a hollow fiber membrane 50. Therefore, this uniform blood flow allows for maximum gas transfer.

The hollow fiber membrane wound bundle 51 is then placed in a clam shell-type cutting fixture and a hot cutting tool is run along the rectilinear end portion 53 of the wound hollow fiber membrane bundle to sever and seal the ends of the individual fibers. The heat seals the lumens of the hollow fibers so that the lumens do not become plugged during the potting procedure described below.

B Heat Exchange

The heat exchanger section 14 includes the region defined by second compartment 40. Compartment 40 includes hollow tube wound bundle 96 comprised of a plurality of hollow tubes 97 formed into a mat as seen in FIG. 4. The individual heat exchange hollow tubes 97 are preferably formed from a polyurethane resin such as B. F. Goodrich Estane TM 58091.

The heat exchange tubes of the present invention preferably have an outside diameter of from approximately about 0.025 inches (635 $\mu$m) to about 0.040 inches (1,016 $\mu$m) and most preferably have an outside diameter of 0.033 inches (840 $\mu$m). The tubes of the present invention also preferably have a wall thickness of from approximately about 0.002 inches 50 $\mu$m) to 0.006 inches (152 $\mu$m) and most preferably have a wall thickness of about 0.004 inches (120 $\mu$m). The formation of heat exchanger tubes from polyurethane rather than the stainless steel used in a variety of commercially available units represents a significant advance because the flexibility of the polyurethane tubes allows the tubes to be formed into a mat and a wound bundle as more fully described below. The wound bundle configuration allows one to reduce the surface area of heat exchange tubing needed to provide efficient heat exchange which thereby reduces prime volume.

In addition, while the efficiency of the heat exchanger is an important design consideration, it is vital that there is no leakage between the water path and blood path. If the design of the oxygenator does not provide for a leak-proof seal between the water and blood paths, hemolysis of red blood cells will result. The use of polyurethane heat exchange tubes (instead of stainless steel coils) and polyurethane end-potting compounds provides a leak-proof seal. The compatibility between the polyurethane tubes and the potting compound thereby greatly increases the effectiveness of the product visa vis patient safety.

A. Hollow Tube Heat Exchanger Wound Bundle

To maximize the performance characteristics of the oxygenator as a whole and to reduce prime volume, the present invention utilizes a hollow tube mat 300 which is then wound into a hollow heat exchange tube bundle 96.

Similar to the knitting and winding of the hollow fiber membranes described above, hollow heat exchange tubes 97 are weft knitted into a mat 300 by a weft knitting machine. A mat is a flat, single-layer arrangement of substantially parallel hollow tubes knitted together in a spaced apart relationship by warp thread means 302, as can be seen in FIG. 4.

The process of weft knitting a mat from a single strand of hollow tubing material is as discussed above for the weft knitting of hollow fiber membranes and therefore will not be repeated here.

Referring again to FIG. 4, hollow tubes 97 are disposed at regular lateral intervals along the entire length of the mat 300. Hollow tubes 97 are knitted together and maintained substantially parallel to each other by warp thread means 302 running transversely to tubes 97. The warp thread means 302 may be a multi-filament thread or ribbon or hollow fiber tape.

The number of tubes per centimeter is preferably from 5.7 to 9.5 tubes per centimeter, and most preferably is about 7.0 tubes per centimeter. It is not necessary for the spacing interval 304 between each hollow tube to be identical so long as it falls within a range of approximately about 0.175 cm to 0.105 cm. The spacing interval is calculated by measuring the distance between center A and center B of hollow tubes 97. In the preferred embodiment, the finished mat 300 is continuous.

The hollow tube heat exchanger wound bundle is obtained by winding the hollow tube mat 300 described above onto a flat-shaped core or plate 214 under a winding tension of preferably 0.2–1.2 lbs and most preferably from 0.3–0.6 lbs. The plate 214 has a plurality of windows 216 which enable transverse perfusion of the hollow tube heat exchanger wound bundle 96 while it is in place in compartment 30. To construct the hollow tube heat exchanger wound bundle 96, the hollow tube mat 300 is partially wound by hand onto plate 214. The plate 214 is placed on a the winding arm of a tensioner/-winding machine. The tension is set at 0.6 lbs and the mat is wound for approximately 8 to 12 full revolutions or until one hollow tube heat exchanger wound bundle 96 contains from about 16 to about 24 layers of plies of the hollow tube mat 300. A hollow tube ply 301 is a cut or continuous fiber mat section formed in the production of the wound bundle 96 per complete revolution of the bundle. Successive layers of hollow tube plies 301 are parallel to each other. The individual hollow tubes 97 that comprise the plies 301 and layers 305 form a pattern of spaced apart interdigitation that allows for the uniform flow of blood thereby increasing heat exchange efficiency.

The number of layers 305 comprised of plies 301 that each hollow tube heat exchanger wound bundle 96 contains may vary within the limits described above depending upon the geometry of the heat exchange compartment into which it is inserted. For example, for the second compartment 40 in accordance with the present invention, a hollow tube heat exchanger wound bundle 96 preferably contains from about 18 to 22 layers of plies. However, if an oxygenator/heat exchanger is not needed as an integrated unit and rather it is desired to construct a nonintegrated heat exchange unit, one may make various changes to the geometry of the heat exchange compartment without deviating from the spirit of the present invention. For example, the width and height of the compartment may be varied and thus fewer than 18 layers of plies or more than 22 layers of plies may be utilized. However, typically in order to have sufficient heat exchange efficiency the layers 305 of hollow tube heat exchanger wound bundle 96 will be approximately from about 16 to 24 layers of plies.

The cross section of the hollow tube heat exchanger wound bundle 96 so formed preferably has the form of a rectangle with rounded corners, a segment of a circle or semi-circle with rounded edges, or an ellipse. These types of shapes produce space-saving configurations and prime volume-reducing wound hollow tube bundles. After the potting procedure described below is completed, the rectangular portion of the hollow tube heat exchanger bundle encompasses the functional area while the rounded edges are non-functional because the higher pack density on the sides causes substantial resistance to flow.

As can be readily seen from FIGS. 4 and 5, the warp thread 302 acts as a spacer between each parallel hollow tube 97 in the mat 300, each hollow fiber ply 301 and all layers 305 of hollow tube plies that comprises the hollow tube heat exchanger wound bundle 96. The advantage of this uniform spaced apart relationship between the individual hollow tubes, each successive hollow tube ply 301 and the layers 305 in the hollow tube heat exchanger wound bundle 96, as seen in FIG. 5, is to control the distribution of blood flow so that it is uniform throughout the hollow tube heat exchanger wound bundle 96. This uniform blood flow allows for high heat exchange efficiency.

The hollow tube heat exchanger wound bundle 96 is then placed in a clam shell-type cutting fixture and a hot cutting tool is run along the rectilinear end portion 55 of the hollow tube heat exchanger wound bundle 96 to sever and seal the ends of the individual tubes. Additionally, prior to potting the heat cut end of the wound tube bundle may be dipped in wax to insure closure of the tube ends so that they do not become plugged during the potting procedure described below.

After the tubing is formed into a mat and wound bundle, the wound bundle is placed in compartment 40. Pack density is determined as above. Preferably, a pack density of between about 45–65% and most preferably between about 52–57% provides an efficient heat exchanger with an acceptable pressure drop.

A diffuser plate 100 is joined to core 20 along legs 42,44 by ultrasonic welding, fusion, heat staking, press fitting, heat welding, or other similar means at points 108. Diffuser plate 100 includes a plurality of chamfered orifices 102 and may be identical to the diffuser plate 60. Second blood plate 110 (which may or may not be ribbed for rigidity) vibration or heat welded onto core 20 further encloses the hollow tube heat exchanger wound bundle as shown in FIGS. 1, 2 and 3. Second blood plate 110 includes a blood inlet port 114 and may include a temperature probe port 116 and sample port 118. As shown in FIG. 6, second blood plate 110, diffuser plate 100 and potting compound 185 define blood distribution manifold 130.

As in the case of the oxygenator diffuser plate 60, the heat exchanger diffuser plate 100 is preferably separated from cover 110 by a plurality of nodes 120. Nodes 120 may be joined to cover 110 and diffuser 100 thereby defining blood distribution manifold 130 therebetween.

In an alternative embodiment, diffuser plate 100 may be deleted. In that case, the hollow tube heat exchanger wound bundle is place in second compartment 40 flush against a distributor blood plate means similar to blood plate 110 to control pack density. Distributor blood plate means (not shown) will have a pattern of V-shaped, X-shaped or diamond shaped grooves cut into the interior side touching the hollow tube heat exchanger wound bundle which serves the same purpose of blood distribution manifold 130, that is to create a path from which the blood can flow. Alternatively, distributor blood plate means can be constructed in a honeycomb pattern or with raised ribs on the interior side thereof, which ribs or honeycomb pattern will have a groove or channel cut into each one or distributor blood plate means may also be constructed with an outwardly extending depression in the surface thereof to create the blood distribution manifold. The elimination of diffuser plate 100 cuts down on production costs while maintaining the desired characteristics.

The oxygenator, including the heat exchange unit and oxygenator unit may then be end potted at each end with a polyurethane potting compound. Centrifugal end potting is well known in the art and is, for example, disclosed in U.S. Pat. No. 4,389,363 to Molthop.

Suitable potting compounds are available from Caschem, Inc. of Bayonne, N.J. A polyurethane casting system of Caschem, Inc. is described in U.S. Pat. No. Re. 31,389. After potting, the hollow fibers and hollow tubes are reopened by conventional techniques such as by slicing through the potted bundle with a sharp knife to expose the interior of the fibers. The potting compound 185 provides a superior seal which provides maximum assurance that the seal will not leak.

The core 20 allows the potting of the heat exchange bundle 96 and the oxygenator bundle 51 to be performed simultaneously. The process of end potting tends to be time consuming and eliminating the need for two separate end potting procedures represents a marked improvement over commercially available units. Also, a single step potting reduces the possibility of leakage around the potted edges.

Referring to FIGS. 1 and 2, blood outlet port 72 and blood inlet port 114 preferably are constructed and arranged such that blood is directed across substantially the width of the fiber and tube bundles in the respective compartments.

Blood flows from the heat exchanger section 40 into the oxygenator section 30 by passing through perforations 140 in center divider 16. Center divider 16 is preferably constructed and arranged as described above for diffuser plate 60 and the same considerations apply as to the number and size of perforations 140.

After the hollow tube heat exchanger wound bundle 96 and hollow fiber membrane wound bundle 51 have been end potted and reopened, the device is completed by attaching first and second headers 160 and 170. Headers 160,170 provide gas and heat exchange media inlets and outlets to the open ends of the hollow fiber membrane wound bundle 51 and the hollow tube heat exchanger wound bundle 96.

First header 160 is secured to the perimeter of the cross-sectional end of core 20 and to first and second blood plates 70 and 110. A gas inlet 162 of first header 160 allows oxygen to contact all of the open hollow fiber membrane ends. A heat exchange media outlet 164 allows heat exchange media leaving the interior of the heat exchange hollow tubes 97 to exit the device.

Second header 170 is constructed in a similar manner to first header 160 and includes a gas outlet 172 which collects gas leaving the open ends of the oxygenator hollow fibers such that gas is exhausted through gas outlet 172. Vent port 178 may also be provided as shown. A heat exchange media inlet 174 provides heat exchange media to the lumens of the heat exchanger hollow tubes 97 through their open ends.

Operation

In operation, blood entering inlet 114 sweeps through manifold 130 and uniformly contacts the heat exchanger bundle after passing through the diffuser 100. Manifold 130, in conjunction with diffuser 100 provides excellent blood flow distribution through the hollow tube heat exchanger wound bundle 96 where the blood is cooled and warmed by liquid entering heat exchange media inlet 174 and passing through the interior lumens of hollow tubes 97 and exiting through heat exchange media outlet 164.

The blood proceeds through the orifices 140 in core 20 and comes into contact with the hollow fiber membrane wound bundle 51 where it is oxygenated by gas entering the lumens of the individual hollow fiber membranes 50 from gas inlet 162 and exiting through gas outlet 172. Oxygenated blood then passes through orifices 62 in diffuser 60 and collects in blood collecting manifold 80. Blood then exits the oxygenator from blood outlet 72 where it is then circulated back to the patient.

Nonintegrated Units.

If an oxygenator is not needed in an integrated unit, the oxygenator features of the invention may be utilized as a separate unit by providing a core having a U-shaped cross-section. Center divider 16 becomes a replacement for diffuser plate 100 and will be supported in a spaced relationship to the outer case. The blood plate would then be secured to the center divider. Of course, first and second headers would only need gas inlets and outlets. The oxygenator thus described provides all of the advantages found in the oxygenator section of the integrated device. It may be used in conjunction with systems having their own separate heat exchange units if desired.

The heat exchanger section described above for the device may be produced as a nonintegrated unit without an oxygenating section. A heat exchanger may be constructed by utilizing a core having a U-shaped cross-section such that center divider 16 is enclosed within blood plate 70. As above, the headers would be modified, in this case to provide heat exchanger media inlets and outlets.

Alternatively, in a fourth embodiment of the present invention one may construct the nonintegrated heat exchanger by providing first and second perforated diffuser plates, first and second blood plates, first and second headers, and a hollow tube heat exchanger wound bundle 97 with potting 185. The first blood plate, first diffuser plate and potting compound 185 would, as in the preferred embodiment of the present invention, define a blood collecting manifold. The second blood plate, second diffuser plate and potting compound 185 would, as above, define a blood distribution manifold. Both manifolds would be created by spacer nodes, again as in the preferred embodiment of the present invention. First and second headers would be modified to provide heat exchanger media inlets and outlets only.

Any application needing heat exchange with the advantages of using the polyurethane hollow tubes described above may be satisfied by following the teachings of the invention. A hollow tube heat exchanger wound bundle may be placed in a case and end potted with a polyurethane end potting compound. After end caps are secured a heat exchanger is formed in which the interior of the hollow tubes are isolated from the flow paths among the outside of the tubes. Heat exchange media may be passed through the lumens or outside the lumens as desired by the application. The heat exchanger may include diffuser plates to increase the distribution of fluid over the tubes. The unique combination of polyurethane hollow tubes with the polyurethane end potting compound provides maximal security that there will not be leakage in the device.

Although the device is shown in the figures with a core having an H-shaped cross-section, the advantage of the invention may also be attained with a device in which the hollow tube heat exchanger wound bundle is generally perpendicular rather than parallel to the hollow fiber membrane wound bundle oxygenator fibers. Such a device may be made by moving the lower portions of legs 43,42 below the center divider to the other edges of the center divider. In such a construction the end caps would need to be separate and two separate end pottings would be required.

Data

The Association for the Advancement of Medical Instrumentation (AAMI) sets the acceptable standard conditions for oxygenator performance characteristics. The performance characteristics of the oxygenator in accordance with the present invention were measured at a total hemoglobin of $12.0\pm1.0$ g/dl; percent oxygen saturation $55.0\pm2.0\%$; partial pressure carbon dioxide $45.0\pm5.0$ mmHg; base excess $0.0\pm2.0$ mmole/L; temperature $37.0°\pm1.0°$ C.; activated clotting time greater than 480 seconds; and platelet count less than 100,000 $\mu$L.

Performance data from units constructed in accordance with the preferred embodiment of the present invention are noted below but are in no way intended to be limiting.

TABLE I

| UNIT | PRIME VOLUME ml | PRESSURE DROP mmHg | OXYGEN TRANSFER ml/min | HEAT EXCHANGE EFFICIENCY % |
|---|---|---|---|---|
| 3329-104-01 | 240 | 110 | 431 | 42.0 |
| 3329-104-02 | 238 | 78 | 423 | 45.0 |
| 3329-103-05 | 245 | 88 | 429 | 44.9 |
| 3329-103-06 | 245 | 108 | 400 | 49.0 |
| 3329-104-03 | 270 | 71 | 406 | 48.0 |
| 3329-104-04 | 265 | 64 | 400 | 47.5 |
| 3329-104-05 | 265 | 62 | 428 | 44.0 |
| 3329-103-07 | 245 | 84 | 407 | 44.3 |
| 3329-103-08 | 250 | 88 | 429 | 44.9 |
| 3329-103-09 | 235 | 105 | 406 | 40.0 |
| 3329-103-10 | 230 | 118 | 376 | 45.5 |
| 3329-103-11 | 215 | 212 | 416 | 47.0 |
| 3329-103-12 | 215 | 162 | 435 | 47.0 |
| 3329-103-01 | 270 | 87 | 413 | 45.0 |
| 3329-103-02 | 275 | 79 | 433 | 49.0 |
| 3329-103-03 | 250 | 100 | 421 | 44.3 |
| 3329-103-04 | 255 | 87 | 426 | 49.5 |
| 3329-105-01 | 235 | 138 | 448 | 46.0 |
| 3329-105-02 | 225 | 103 | 430 | 46.5 |
| 3329-105-03 | 240 | 104 | 431 | 51.5 |
| 3329-105-04 | 225 | 148 | 447 | 48.5 |
| 3329-105-05 | 235 | 108 | 451 | 45.0 |
| 3329-105-06 | 245 | 93 | 426 | 50.5 |

Although a description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. An integrated heat exchanger and oxygenator device comprising:
   (a) a housing, said housing including first and second diffuser plates, a core with a perforated center divider having first and second opposing side walls, said core and said first diffuser plate together defining a first compartment and said core and said second diffuser plate together defining a second compartment;
   (b) a hollow fiber membrane wound bundle disposed within said first compartment including a plurality of hollow fiber membranes each defining a central lumen, said hollow fiber membrane wound bundle defining first and second hollow fiber end regions; and
   (c) a hollow tube heat exchanger wound bundle disposed within said second compartment including a plurality of hollow tubes each defining a central lumen, said hollow tube heat exchanger wound bundle defining first and second hollow tube end regions;
   (d) said hollow fiber end regions and hollow tube end regions being encapsulated with a potting compound which bonds to said first and second side walls;
   (e) first and second headers joined to said first and second opposing side walls;
   (f) first and second blood plates each joined to said opposing side walls of said core on opposite ends thereof, wherein said first blood plate, said first diffuser plate and said potting compound define a blood collecting manifold and wherein said second blood plate, said second diffuser plate and said potting compound define a blood distribution manifold;
   (g) a blood inlet in fluid communication with said blood distribution manifold;
   (h) a blood outlet in fluid communication with said blood collecting manifold;
   (i) a heat exchanger media inlet and a heat exchanger media outlet in fluid communication with the lumens of said hollow tubes; and
   (j) a gas inlet and a gas outlet in communication with the lumens of said hollow fiber membranes.

2. The integrated heat exchanger and oxygenator device of claim 1 wherein said hollow tube heat exchanger wound bundle further comprises a hollow tube mat including a plurality of substantially parallel hollow tubes knitted together by warp thread means in a spaced apart relationship, said hollow tube mat forming layers of stacked, substantially parallel plies wherein said plurality of substantially parallel hollow tubes form a pattern of interdigitation within said hollow tube heat exchanger wound bundle.

3. The integrated heat exchanger and oxygenator device of claim 1 wherein said hollow fiber membrane wound bundle further comprises a hollow fiber mat including a plurality of substantially parallel hollow fiber membranes knitted together by warp thread means in a spaced apart relationship, said hollow fiber mat forming layers of stacked, substantially parallel plies wherein said plurality of substantially parallel hollow fiber membranes form a pattern of interdigitation within said hollow fiber membrane wound bundle.

4. The integrated heat exchanger and oxygenator device of claim 1 wherein said hollow tube heat exchanger wound bundle further comprises a hollow tube mat including a plurality of substantially parallel hollow tubes knitted together by warp thread means in a spaced apart relationship, said hollow tube mat forming layers of stacked, substantially parallel plies wherein said plurality of substantially parallel hollow tubes form a pattern of interdigitation within said hollow tube heat exchanger wound bundle and wherein said hollow fiber membrane wound bundle further comprises a hollow fiber mat including a plurality of substantially parallel hollow fiber membranes knitted together by warp thread means in a spaced apart relationship, said hollow fiber mat forming layers of stacked, substantially parallel plies wherein said plurality of substantially parallel hollow fiber membranes form a pattern of interdigitation within said hollow fiber membrane wound bundle.

5. The integrated heat exchanger and oxygenator device of claim 4 wherein said stacked layers of hollow fiber mat comprise from about 80 to about 120 substantially parallel plies.

6. The integrated heat exchanger and oxygenator device of claim 3 wherein said stacked layers of hollow fiber mat comprise from about 80 to about 120 substantially parallel plies.

7. The integrated heat exchanger and oxygenator device in accordance with claim 5 wherein said hollow fiber mat comprises from about 15 to about 21 hollow fiber membranes per centimeter.

8. The integrated heat exchanger and oxygenator device in accordance with claim 2 wherein said warp thread means comprise a multifilament warp thread.

9. The integrated heat exchanger and oxygenator device in accordance with claim 2 wherein said hollow tube mat comprises from about 5.7 to about 9.5 hollow tubes per centimeter.

10. The integrated heat exchanger and oxygenator device in accordance with claim 2 wherein an interval spacing between said hollow tubes is from about 0.175 cm to about 0.105 cm.

11. The integrated heat exchanger and oxygenator device in accordance with claim 2 wherein said hollow tube heat exchanger wound bundle comprises from about 18 to about 22 layers of said substantially parallel plies.

12. The integrated heat exchanger and oxygenator device in accordance with claim 2 wherein a measured packing density of said hollow tube heat exchanger wound bundle is from about 45% to about 65%.

13. The integrated heat exchanger and oxygenator device in accordance with claim 3 wherein a measured packing density of said hollow fiber membrane wound bundle is from about 50% to about 60%.

14. A nonintegrated heat exchanger comprising:
   (a) a housing, said housing including first and second perforated diffuser plates having first and second opposing side walls, said first and second diffuser plates and said first and second opposing side walls defining a heat exchange compartment;
   (b) a hollow tube heat exchanger wound bundle disposed within said heat exchange compartment, said hollow tube heat exchanger wound bundle including a plurality of hollow tubes each defining a central lumen, said hollow tube heat exchanger wound bundle having first and second hollow tube end regions;

(c) said hollow tube end regions being encapsulated with a potting compound which bonds to said first and second side walls;

(d) first and second blood plates each joined to said opposing side walls of said diffuser plates, wherein said first blood plate, said first diffuser plate and said potting compound define a blood collecting manifold and wherein said second blood plate, said second diffuser plate and said potting compound define a blood distribution manifold;

(e) a blood inlet in fluid communication with said blood distribution manifold;

(f) a blood outlet in fluid communication with said blood collecting manifold; and (g) a heat exchanger media inlet and a heat exchanger media outlet in fluid communication with the lumens of said hollow tubes.

15. The nonintegrated heat exchanger device in accordance with claim 14, wherein said hollow tube heat exchanger wound bundle further comprises a hollow tube mat including a plurality of substantially parallel hollow tubes knitted together by warp thread means in a spaced apart relationship, said hollow tube mat forming layers of stacked, substantially parallel plies wherein said plurality of substantially parallel hollow tubes form a pattern of interdigitation within said hollow tube heat exchanger wound bundle.

16. The nonintegrated heat exchanger device in accordance with claim 15 wherein said warp thread means comprise a multifiliment warp thread.

17. The nonintegrated heat exchanger device in accordance with claim 15 wherein said hollow tube mat comprises from about 5.7 to about 9.5 hollow tubes per centimeter.

18. The nonintegrated heat exchanger device in accordance with claim 15 wherein an interval spacing between said hollow tubes is from about 0.175 cm to about 0.105 cm.

19. The nonintegrated heat exchanger device in accordance with claim 15 wherein said hollow tube heat exchanger wound bundle comprises from about 16 to about 24 layers of said substantially parallel plies.

20. The nonintegrated heat exchanger device in accordance with claim 15 wherein a measured packing density of said hollow tube heat exchanger wound bundle is from about 45% to about 65%.

21. An integrated heat exchanger and oxygenator device comprising:

(a) a housing, said housing including distributor blood plate means, a diffuser plate, a core with a perforated center divider having first and second opposing side walls, said core and said diffuser plate together defining a first compartment and said core and said distributor blood plate means together defining a second compartment;

(b) a hollow fiber membrane wound bundle disposed within said first compartment including a plurality of hollow fiber membranes each defining a central lumen, said hollow fiber membrane wound bundle defining first and second hollow fiber end regions; and (c) a hollow tube heat exchanger wound bundle disposed within said second compartment including a plurality of hollow tubes each defining a central lumen, said hollow tube heat exchanger wound bundle defining first and second hollow tube end regions;

(d) said hollow fiber end regions and hollow tube end regions being encapsulated with a potting compound which bonds to said first and second side walls and a first blood plate and said distributor blood plate means;

(e) first and second headers joined to said first and second opposing side walls and said first blood plate and said distributor blood plate means;

(f) said first blood plate and said distributor blood plate means each joined to said opposing side walls of said core on opposite ends thereof, wherein said first blood plate, said diffuser plate and said potting compound define a blood collecting manifold and wherein said distributor blood plate means and said potting compound define a blood distribution manifold;

(g) a blood inlet in fluid communication with said blood distribution manifold;

(h) a blood outlet in fluid communication with said blood collecting manifold;

(i) a heat exchanger media inlet and a heat exchanger media outlet in fluid communication with the lumens of said hollow tubes; and (j) a gas inlet and a gas outlet in communication with the lumens of said hollow fiber membranes.

22. The integrated heat exchanger and oxygenator device of claim 21 wherein said hollow tube heat exchanger wound bundle further comprises a hollow tube mat including a plurality of substantially parallel hollow tubes knitted together by warp thread means in a spaced apart relationship, said hollow tube mat forming layers of stacked, substantially parallel plies wherein said plurality of substantially parallel hollow tubes form a pattern of interdigitation within said hollow tube heat exchanger wound bundle.

23. The integrated heat exchanger and oxygenator device of claim 21 wherein said hollow fiber membrane wound bundle further comprises a hollow fiber mat including a plurality of substantially parallel hollow fiber membranes knitted together by warp thread means in a spaced apart relationship, said hollow fiber mat forming layers of stacked, substantially parallel plies wherein said plurality of substantially parallel hollow fiber membranes form a pattern of interdigitation within said hollow fiber membrane wound bundle.

24. The integrated heat exchanger and oxygenator device of claim 21 wherein said hollow tube heat exchanger wound bundle further comprises a hollow tube mat including a plurality of substantially parallel hollow tubes knitted together by warp thread means in a spaced apart relationship, said hollow tube mat forming layers of stacked, substantially parallel plies wherein said plurality of substantially parallel hollow tubes form a pattern of interdigitation within said hollow tube heat exchanger wound bundle and wherein said hollow fiber membrane wound bundle further comprises a hollow fiber mat including a plurality of substantially parallel hollow fiber membranes knitted together by warp thread means in a spaced apart relationship, said hollow fiber mat forming layers of stacked, substantially parallel plies wherein said plurality of substantially parallel hollow fiber membranes form a pattern of interdigitation within said hollow fiber membrane wound bundle.

25. The integrated heat exchanger and oxygenator device of claim 24 wherein said stacked layers of hollow fiber mat comprise from about 80 to about 120 substantially parallel plies.

26. The integrated heat exchanger and oxygenator device of claim 23 wherein said stacked layers of hollow fiber mat comprise from about 80 to about 120 substantially parallel plies.

27. The integrated heat exchanger and oxygenator device in accordance with claim 25 wherein said hollow fiber mat comprises from about 15 to about 21 hollow fiber membranes per centimeter.

28. The integrated heat exchanger and oxygenator device in accordance with claim 22 wherein said warp thread means comprise a multifilament warp thread.

29. The integrated heat exchanger and oxygenator device in accordance with claim 22 wherein said hollow tube mat comprises from about 5.7 to about 9.5 hollow tubes per centimeter.

30. The integrated heat exchanger and oxygenator device in accordance with claim 22 wherein an interval spacing between said hollow tubes is from about 0.175 cm to about 0.105 cm.

31. The integrated heat exchanger and oxygenator device in accordance with claim 22 wherein said hollow tube heat exchanger wound bundle comprises from about 18 to about 22 layers of said substantially parallel plies.

32. The integrated heat exchanger and oxygenator device in accordance with claim 22 wherein a measured packing density of said hollow tube heat exchanger wound bundle is from about 45% to about 65%.

33. The integrated heat exchanger and oxygenator device in accordance with claim 23 wherein a measured packing density of said hollow fiber membrane wound bundle is from about 50% to about 60%.

* * * * *

UNITED STATES PATENT AND TRADEMARK OFFICE
CERTIFICATE OF CORRECTION

PATENT NO. : 5,429,184
DATED : July 4, 1995
INVENTOR(S) : Bach, et al.

It is certified that error appears in the above-indentified patent and that said Letters Patent is hereby corrected as shown below:

Column 9, line 18, delete "Exchange"  substitute --Exchanger--
Column 9, line 33, delete "50 µm)"    substitute --(50 µm)--
Column 9, line 56, delete "visa"      substitute --vis a-- therefor.

Signed and Sealed this

Twelfth Day of December, 1995

Attest:

BRUCE LEHMAN

*Attesting Officer*   *Commissioner of Patents and Trademarks*